(12) United States Patent
Magrini et al.

(10) Patent No.: US 6,315,852 B1
(45) Date of Patent: Nov. 13, 2001

(54) PRODUCTION PROCESS OF VARYING THICKNESS OSTEOSYNTHESIS PLATES

(75) Inventors: Anna Magrini, Via Brigata Salerno 2/1, Genoa (IT), 16147; Maurizio Carta, Genoa (IT)

(73) Assignee: Anna Magrini, Genoa (IT)

( * ) Notice: Subject to any disclaimer, the term of this patent is extended or adjusted under 35 U.S.C. 154(b) by 0 days.

(21) Appl. No.: 09/269,151

(22) PCT Filed: Sep. 1, 1997

(86) PCT No.: PCT/IT97/00217

§ 371 Date: Feb. 26, 1999

§ 102(e) Date: Feb. 26, 1999

(87) PCT Pub. No.: WO98/09578

PCT Pub. Date: Mar. 12, 1998

(30) Foreign Application Priority Data

Sep. 4, 1996 (IT) ................................. GE96A0076

(51) Int. Cl.[7] ................................... B32B 31/18
(52) U.S. Cl. ................ 156/248; 156/250; 156/267; 156/268; 83/13; 83/14; 83/31; 83/953
(58) Field of Search .................... 156/248, 267, 156/268, 250; 83/13, 14, 31, 929, 953

(56) References Cited

U.S. PATENT DOCUMENTS

| | | | |
|---|---|---|---|
| 3,894,633 | * | 7/1975 | Egan et al. . |
| 4,391,168 | * | 7/1983 | Gerber et al. . |
| 4,683,878 | * | 8/1987 | Carter . |
| 5,458,717 | * | 10/1995 | Kurita ................................. 83/31 X |
| 5,822,865 | * | 10/1998 | Bosch et al. . |

FOREIGN PATENT DOCUMENTS 0 266 146 * 5/1988 (EP) .

* cited by examiner

*Primary Examiner*—Curtis Mayes

(57) ABSTRACT

The invention concerns a process for the production of osteosynthesis plates with a varying thickness to whatever degree. The plates are manufactured by a metal cutting process carried out on a composite structure made by a layer of the material which will form the osteosynthesis plate, bound through a layer of adhesive to a supporting layer with high thermal conductivity and mechanical strength. When the cutting process terminates, the osteosynthesis plate is separated from the supporting layer by heating the composite structure until the adhesive melts or by using a thinner suitable for the adopted adhesive.

1 Claim, 1 Drawing Sheet

4 ALUMINIUM SHEET

3
TITANIUM SHEET

PRODUCTION PROCESS OF VARYING THICKNESS OSTEOSYNTHESIS PLATES

TECHNICAL FIELD

The invention relates to a process for the production of plates for osteosynthesis with a varying thickness thin to whatever degree.

BACKGROUND ART

Plates which are presently used to achieve osteosynthesis have a constant thickness due to the adopted production process. Said process consists in cutting, usually by laser, the plate from a sheet of biocompatible metal characterised by a constant thickness, following the plate contour, and in making the countersink holes for the screws heads by plastic deformation of the metal around the holes.

Osteosynthesis plates with constant thickness should have a thickness dimensioned in order to bear the tension in the most stressed section near the fracture or osteotomy line (proximal area). This thickness is however greater than the thickness required by the stress present in the sections farther from proximal area (distal areas). In these areas the adjustment of the plate to the bone surface done by bending can therefore be more difficult than needed. Another consequence of the constant thickness is that in the distal areas the elastic component of the deformation adopted to fit the plate to the bone geometry is greater than that resulting from a smaller thickness; unwanted stresses and displacements of the bone segments connected by the plate may be experienced.

In general the complex shape, the small size, the limited thickness in the proximal and distal areas of the plate make difficult the manufacturing of plates by metal cutting processes which would be necessary to obtain varying thickness, unless a system for fixing adequately the machined plate is available.

Fixing systems of magnetic type do not work with biocompatible materials such as titanium and stainless steel generally used for osteosynthesis plates. Other clamping systems of mechanical type in which the fastening is carried out by pressure on the workpiece do not permit to machine the plate without interruptions for changing the clamping zone and completing the operation in the plate areas previously hidden by the clamping device. The mechanical fastening doesn't prevent deformation and fracture in the plate areas with a small thickness since cutting loads can create stress conditions which cannot be allowed by the strength of the plate material. Moreover mechanical clamping may leave marks on the surface of the ductile materials used for the production of plates.

Fixing the workpiece by embedding in resin has the disadvantage of a poor dissipation of the heat produced during the workpiece cutting due to the inadequate thermal conductivity of the resin. Consequently the resin temperature increases determining the softening of the resin and the reduction of the resin binding capability necessary to keep the workpiece during the cutting process.

These drawbacks impede the industrial manufacturing by means of metal cutting processes, of osteosynthesis plates with a varying thickness and therefore prevent the achievement of the biomechanical advantages coming from the variation of the plate thickness.

DISCLOSURE OF INVENTION

According to the invention these problems are solved by making a composite structure consisting of a plate of the material which will form the osteosynthesis plate, of (structural) adhesive and of a bearing plate with an adequate strength and high thermal conductivity able to dissipate the heat produced during the cutting, so that from this composite structure, once the desired shape and thickness profile of the osteosynthesis plate have been obtained by a metal cutting process, the osteosynthesis plate could be separated from the bearing plate by melting the adhesive through the heating of the composite structure to a temperature greater than 80° C. or through a thinner.

The invented process is based on the fact that the composite structure manufactured in the said way, gives to the layer of the material which will become the osteosynthesis plate, a structural strength able to resist to the stress produced by the metal cutting. The size of the composite structure can be set in such a way to permit the mechanical clamping of the composite structure to the machine tool by using commercially available fixing devices. The heat generated by the metal cutting is dissipated by the bearing layer thank to its high thermal conductivity, avoiding in this way the heating of the adhesive layer above temperature at which the softening of the adhesive begins. The final separation of the plate from the bearing layer is carried out by exploiting the softening of the adhesive layer which usually for structural adhesives appears at temperature over 80° C. Otherwise it is possible to melt the adhesive layer by adopting a thinner suitable for the employed adhesive.

The main advantage of the invented process consists in making possible the production of osteosynthesis plate with a varying thickness, thin to whatever degree, by adopting a metal cutting machining overcoming the above mentioned technological problems due to the fixing of the plate by clamping or by embedding in resin. Another important intent of the invention consists in making possible the manufacture of osteosynthesis plates with a varying thickness characterised by a better fitting to the bone surface. Another important aim of the invention consists in making possible the manufacture of osteosynthesis plates with varying thickness giving limited stress and relative displacements of the connected bone segments. The invented process permits moreover the production of osteosynthesis plates with a varying thickness in an easy and economical way without the need of complex technologies and skilled labour.

BEST MODE OF CARRYING OUT THE INVENTION

Figure 1:
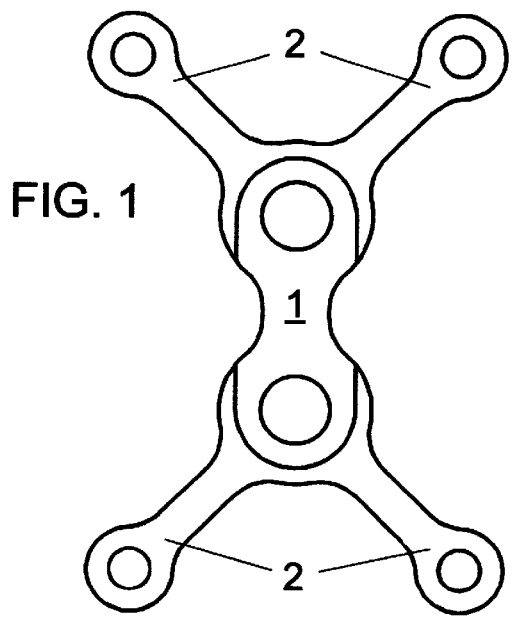
FIG. 1 and FIG. 2 show respectively the plan view and the lateral view of an example of an osteosynthesis plate which can be manufactured by the invented process.
Figure 2:
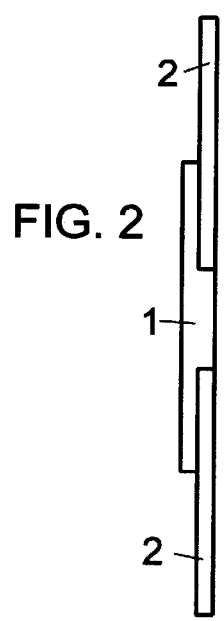
Figure 3:
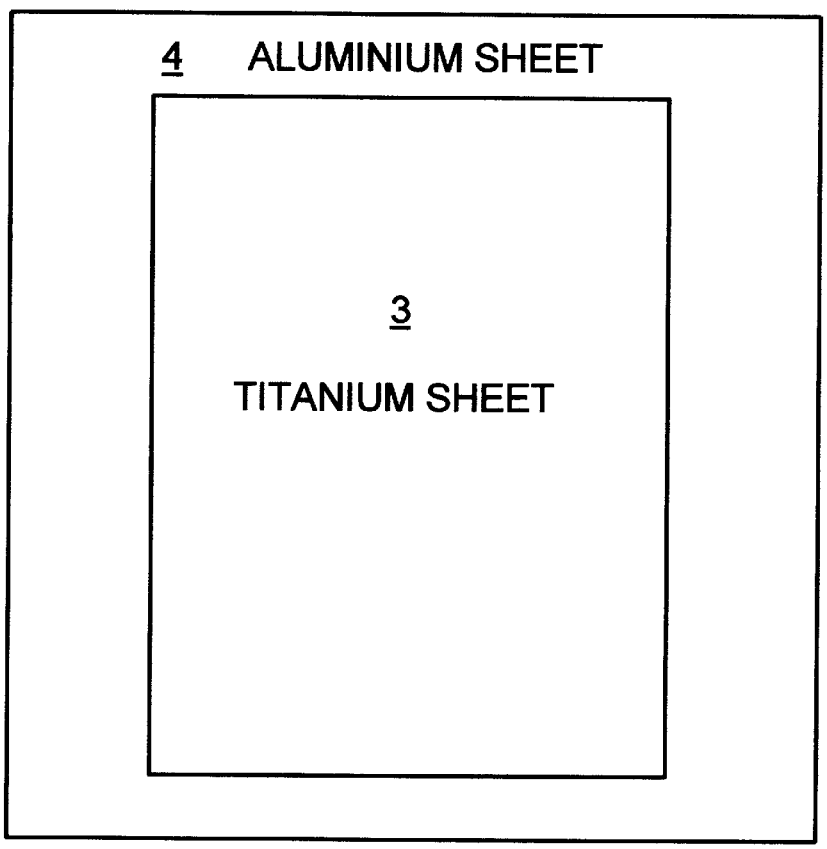
FIG. 3 and FIG. 4 display respectively the plan view and the cross sectional view of the composite structure which is machined in order to manufacture the osteosynthesis plate.
Figure 4:
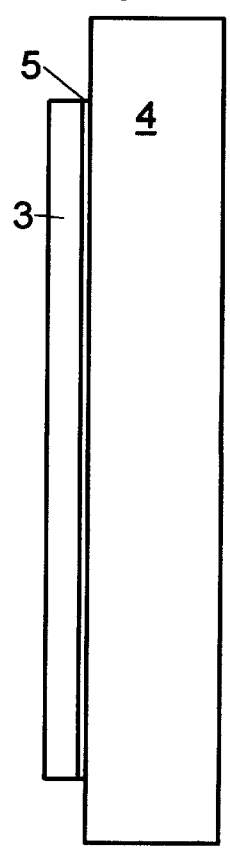

The best mode of carrying out the invented process is described considering the manufacturing of the osteosynthesis plate with reference to the accompanying drawings. The plate material is commercially pure titanium. The shape of the plate, indicated in FIG. 1, is an example of an osteosynthesis plate with a double Y configuration characterised by different thickness in the proximal area 1 and in the distal areas 2. Thickness in the proximal area is 1.00 mm, thickness in the distal areas is 0.50 mm. The production process requires to manufacture the composite structure (FIGS. 3, 4) consisting of a commercially pure titanium sheet (3) with a thickness of 1.05 mm, bound by a cyanoacrylate layer (5) to an aluminium sheet (4). The aluminium sheet is larger than the titanium plate, and its thickness is 4 mm. The composite structure is clamped to the worktable of a milling machine which performs the drilling operations, the surfaces generation according to the required thickness, the contouring of the plate cutting completely the titanium layer. Once the machining has been carried out, the osteosynthesis titanium plate is separated from the bearing aluminium layer by heating the composite structure at a temperature greater than 80° C. in order to melt the adhesive layer.

Alternative ways of carrying out the invented process include other biocompatible plate materials, other bearing plate materials with high thermal conductivity, other types of structural adhesives, other thickness of the composite structure layers, other compatible heating temperatures or alternatively an adhesive thinner.

What is claimed is:

1. A process for maufacturing an osteosynthesis plate with a varying thickness profile comprising the following steps:

a) joining a metallic biocompatible plate to a metallic bearing plate using a structural adhesive to make a composite structure, the structural adhesive having a melting point greater than 80° C. and the metallic bearing plate having a thermal conductivity sufficient to dissipate heat generated by cutting the metallic biocompatible plate of the composite structure such that the temperature of the structural adhesive during cutting is kept below 80° C.;

b) machining the metallic biocompatible plate of the composite structure by a metal cutting process that uses drilling and end milling operations to cut the metallic biocompatible plate into the osteosynthesis plate of varying thickness profile, wherein the metallic bearing plate dissipates heat generated during the metal cutting process to keep the temperature of the structural adhesive of the composite structure below 80° C.; and c) heating the structural adhesive of the composite structure to a temperature greater than 80° C. to melt the structural adhesive to separate the osteosynthesis plate from the metallic bearing plate.

* * * * *